United States Patent [19]

Reher

[11] Patent Number: 5,074,783

[45] Date of Patent: Dec. 24, 1991

[54] ORTHODONTIC BRACKET COATED WITH WATER-SOLUBLE DYE

[75] Inventor: James F. Reher, Pomona, Calif.

[73] Assignee: Ormco Corporation, Glendora, Calif.

[21] Appl. No.: 437,199

[22] Filed: Nov. 16, 1989

[51] Int. Cl.[5] ............ A61C 3/00

[52] U.S. Cl. ............ 433/8; 433/24

[58] Field of Search ............ 433/8, 9, 10, 11, 12, 433/13, 14, 15, 16, 3, 24

[56] References Cited

U.S. PATENT DOCUMENTS

| | | | |
|---|---|---|---|
| 3,496,637 | 2/1970 | Etengoff | 433/8 |
| 4,050,156 | 9/1977 | Chasanoff et al. | 433/8 |
| 4,134,208 | 1/1979 | Pearlman | 433/8 |
| 4,299,569 | 11/1981 | Frantz | 433/8 |
| 4,415,330 | 12/1983 | Daisley et al. | 433/8 |
| 4,551,096 | 11/1985 | Dellinger | 433/24 |
| 4,626,208 | 12/1986 | Hall | 433/3 |
| 4,819,316 | 4/1989 | Rossini et al. | 433/8 |
| 4,952,141 | 8/1990 | Wool | 433/8 |

FOREIGN PATENT DOCUMENTS

| | | | |
|---|---|---|---|
| 2903768 | 8/1980 | Fed. Rep. of Germany | 433/8 |

*Primary Examiner*—John J. Wilson

*Attorney, Agent, or Firm*—Marjama & Pincelli

[57] ABSTRACT

An orthodontic bracket, a method of manufacture and method of installing the bracket. The bracket is provided with visually enhanced reference edges for assisting in alignment of the bracket with respect to the tooth.

23 Claims, 5 Drawing Sheets

ORTHODONTIC BRACKET COATED WITH WATER-SOLUBLE DYE

The present invention relates generally to orthodontic brackets.

BACKGROUND OF THE INVENTION

It is well accepted in the field of orthodontia that each tooth has a particular location in the arch and at a preferred angle between its long axis and the occlusal plane. In the normal practice of orthodontics, an orthodontic archwire is used to apply a force to cause irregular teeth to move in a desired direction. The archwire is secured to orthodontic brackets which are typically bonded directly to the surface of the tooth. It is important that these type brackets be bonded as accurately as possible to the tooth in the desired orientation. In this regard it has been suggested in the prior art to provide the outer configuration of the bracket with certain features for alignment with the anatomy of the tooth and occlusal plane. U.S. Pat. No. 4,415,330 is an example of a prior art bracket wherein the configuration of the bracket is used to properly orient and place the bracket on the tooth.

Recently, in the field of orthodontics, aesthetically pleasing brackets have become increasingly popular. Typically these brackets are made of a material which is transparent, translucent or of a color substantially the same as the tooth. Therefore, these type orthodontic brackets are much more difficult to see with respect to the tooth. While the configuration of the bracket as illustrated in the '430 patent does provide assistance in orienting and placement of these brackets on tooth, the color or lack thereof of these brackets has made it more difficult to view. Additionally, orthodontic brackets have been becoming increasingly smaller in size making viewing even more difficult.

Applicant has invented an improved orthodontic bracket having means for enhancing the visual contrast of the bracket to assist in the alignment and placement of the bracket on the tooth.

SUMMARY OF THE INVENTION

In one aspect of the invention there is provided an orthodontic bracket having a front labial face. The front face having at least one reference edge for alignment with a first reference plane and at least one second reference edge for alignment with a second reference plane. Means are provided for enhancing the visual contrast of the first and second reference edges with respect to the tooth so as to enhance the visibility of the first and second reference edges.

In another aspect of the present invention there is provided a method of making an orthodontic bracket comprising the steps of:

(a) providing an orthodontic bracket with a front labial face having at least one reference edge for alignment, with a first reference plane and at least one second reference edge for alignment with respect to a second reference plane; and (b) placing a removable surface layer on the front labial face, the surface layer having a color which is distinct in appearance with respect to said tooth.

In still another aspect of the present invention there is provided a method of installing an orthodontic bracket on a tooth in a patient. The orthodontic bracket has a front labial face which has at least one reference edge for alignment with a first reference plane and at least one second reference edge for alignment with a second reference plane. The bracket also includes means for enhancing the visibility of the first and second reference edge with respect to said tooth, the method comprising the steps of:

(a) securing the orthodontic bracket on the tooth of a patient using the first and second reference edges for alignment with the first and second reference planes, respectively; and (b) removing the means for enhancing the visibility of the first and second reference edges.

In a further aspect of the present invention there is provided an orthodontic bracket for placement on a tooth. Removable means are provided on the front labial face of the bracket for providing at least one reference edge for alignment with a first reference plane and a second reference edge for alignment with a record second reference plane.

DETAILED DESCRIPTION OF THE INVENTION

Figure 1:
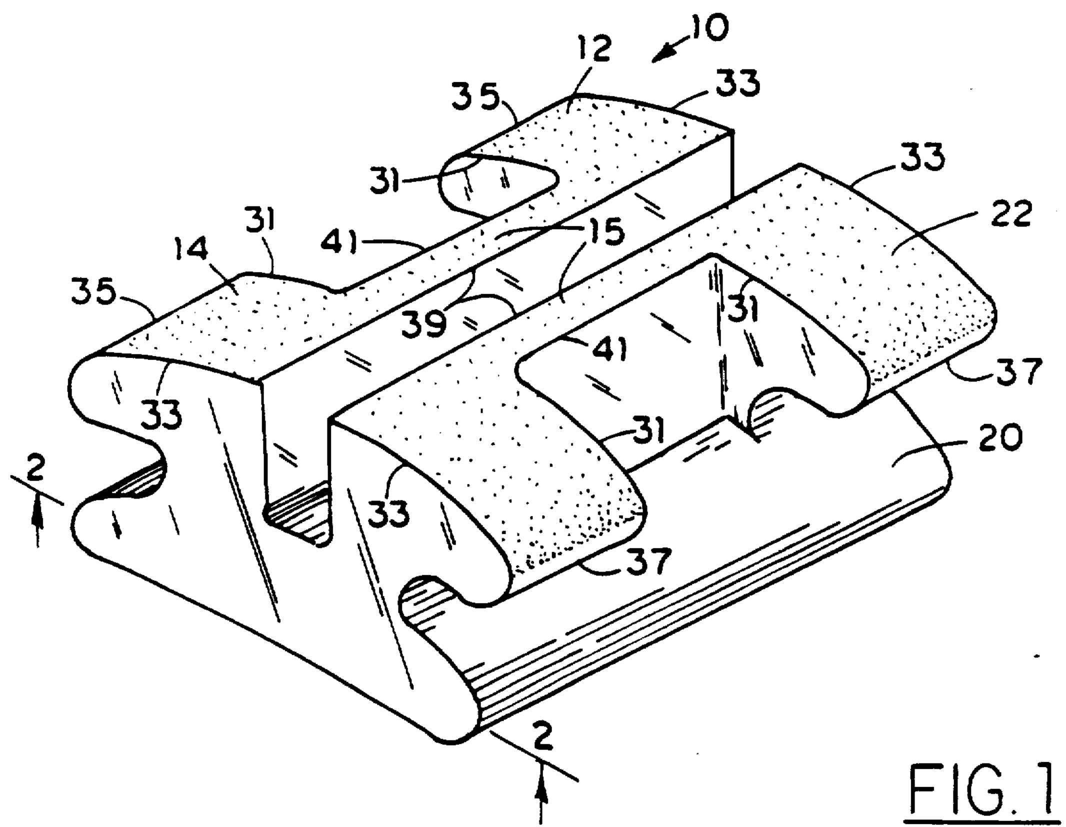
FIG. 1 is an enlarged perspective view of an orthodontic bracket made in accordance with the present invention.
Figure 1A:
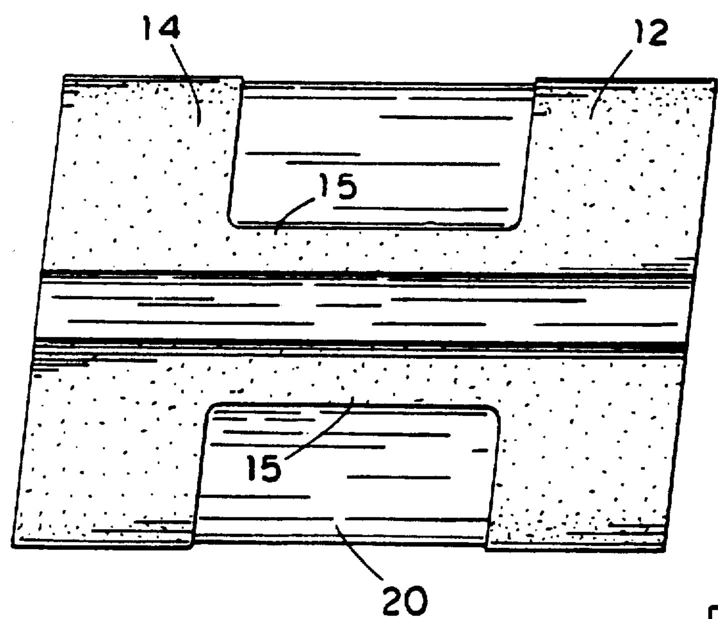
FIG. 1A is a front elevational view of the bracket of FIG. 1.
Figure 2:
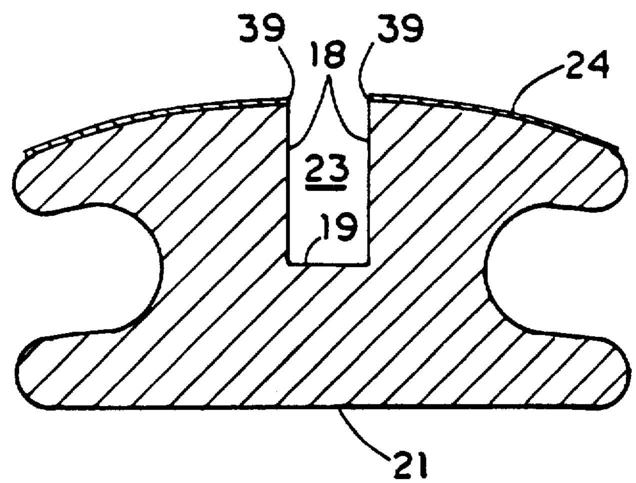
FIG. 2 is a cross-sectional view of the bracket of FIG. 1 taken along line 2—2.
Figure 3:
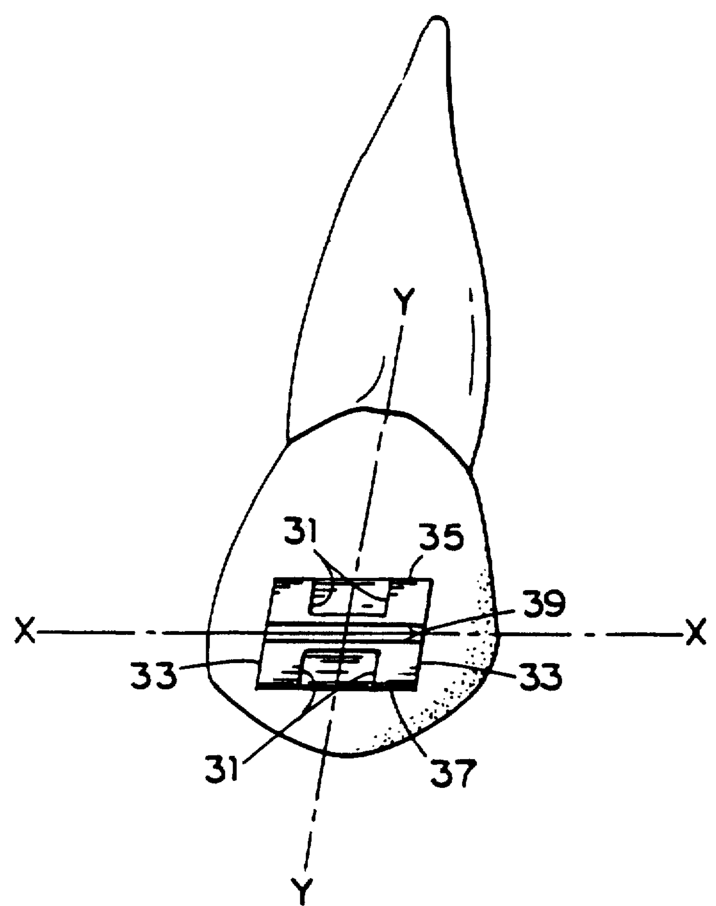
FIG. 3 is a front elevational view of the bracket of FIG. 1 illustrating the bracket in relationship to its position against the tooth in which it is to be secured.

Referring to FIGS. 1-3 there is illustrated an orthodontic bracket 10 made in accordance with the present invention. In the embodiment illustrated the bracket is made of a translucent or transparent material and in the particular embodiment illustrated, bracket 10 is made of polycrystalline alumina material. However, it is to be understood that bracket 10 may be made of any crystalline or non-crystalline material desired. Bracket 10 comprises of a pair of tiewings 12, 14, respectively, and connecting portions which are supported by base 20 having a tooth contact surface 21 for attachment to the tooth. The tiewings 12, 14 and connecting portions 15 form a pair of opposed sidewalls 18 which forms an archwire slot 20 for receiving an orthodontic archwire (not shown) as is typically done in prior art. A substantially flat bottom wall 19 connects sidewalls 18 and form the bottom of slot 20. It should be understood that the bracket 10 may be of any desired configuration used in the prior art or that may be developed with the configuration illustrated in FIG. 1 being for the purpose of illustration only.

The tiewings 12, 14 and connecting portions 15 provides a front labial face 22 which faces the inside portion of the adjacent lips of a patient. For the purpose of the present invention, the front labial face of the bracket shall be considered that portion of the surface of the tracket, as viewed in a front elevational view of the bracket as illustrated in FIG. 3, which faces the labial side of the patient. The labial face 22 is bounded at its perimeter by outer tiewing edges 33, inner tiewing edges 31, top tiewing edges 35, bottom tiewing edges 37, slot edges 39 and edge 41. Bracket 10 is provided with a removable layer 24 which is made of a material having a color which is in visual contrast with that of the adjacent tooth upon which the orthodontic bracket 10 is to be secured. In the particular embodiment illustrated, removable layer 24 is made of a non-toxic black-colored water-soluble ink which has been applied to the front labial face of the bracket. Suitable dyes or inks may be purchased from the Markem Corporation of Keene, NH. It is, of course, understood that various other colors may be used, for example, but not limited to, pink, red, green, so long as substantial visual contrast in color is provided with respect to the tooth. Florescent type colors are quite suitable for this purpose.

At least one edge of labial face 22 is parallel to the longitudinal axis y—y of the tooth and at least one reference edge which is substantially parallel to the occlusal plane of the patient as represented by line x—x in FIG. 3. The longitudinal axis y—y is a well-known referenced plane which is approximated by visualizing the long axis of the crown and only the visual component of the tooth. The bracket 10 has at least one referenced edge which is parallel to the occlusal plane and one reference edge is substantially parallel to the longitudinal axis y—y of the tooth. For a complete understanding of these reference edges, Applicant hereby incorporates by reference U.S. Pat. No. 4,415,330 which describes an orthodontic bracket having a plurality of reference edges which are parallel with either the occlusal of longitudinal axis of the tooth. In the particular embodiment illustrated, edges 31 and 33 are substantially parallel to the longitudinal axis at y—y of the tooth and edges 35, 37, 39 and 41 are all substantially parallel to the occlusal plane x—x of the patient. In the particular embodiment illustrated, it can be seen that the entire perimeter of the front face 22 has an edge which is parallel either to the occlusal plane or longitudinal axis of the tooth. The outer layer 24 completely fills the area within this perimeter. Thus, since the layer 24 is made of a highly visible-colored material with respect to the color of the tooth, the reference edges can be more readily viewed by the orthodontists. It should be understood that the present invention is not limited to the particular configuration bracket illustrated in FIGS. 1-3, nor is the bracket required to have as many reference edges as illustrated in the referenced embodiment. While the preferred embodiment illustrates all of the edges being substantially parallel to either the x—x or y—y plane, only as many edges necessary for alignment with each axis need be highlighted.

Figure 4:
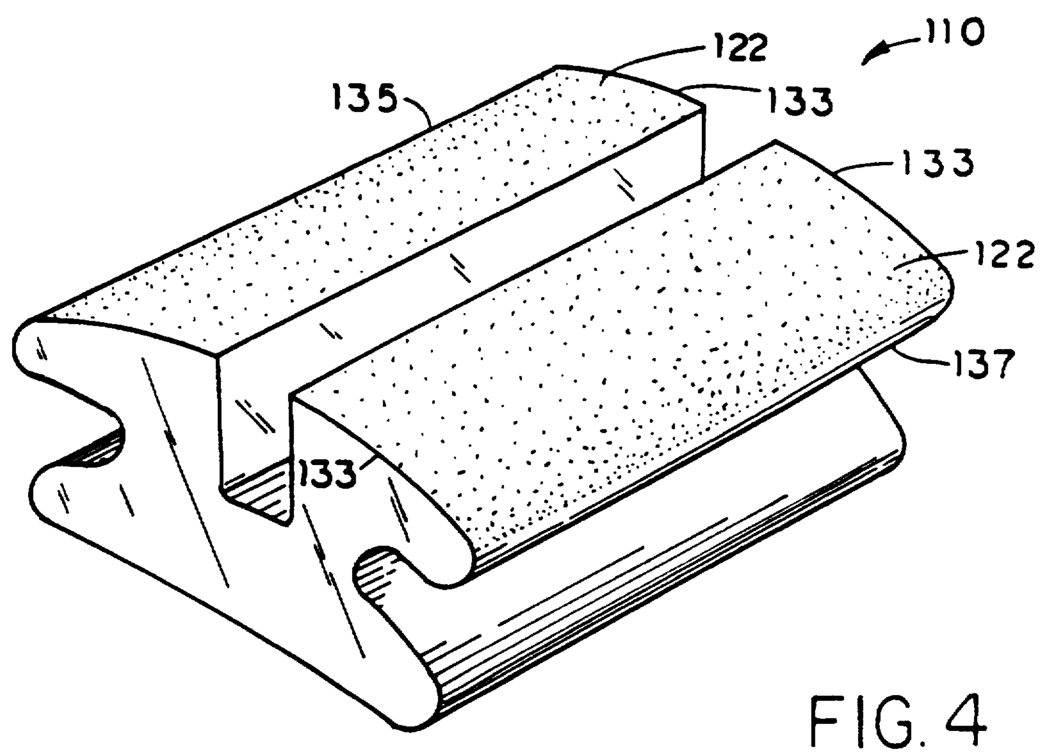
FIG. 4 is a perspective view of a modified orthodontic bracket made in accordance with the present invention.
Figure 4A:
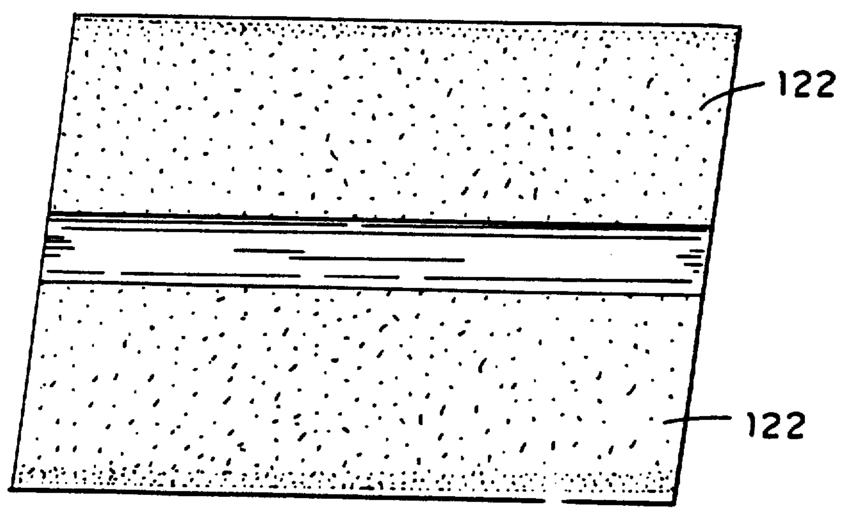
FIG. 4A is a front elevational view of the bracket of FIG. 4.

Referring to FIG. 4, there is illustrated a modified orthodontic bracket 110 made in accordance with the present invention. In this particular embodiment there is illustrated a single wing-type bracket, and thus, does not have connecting portions 15 nor inside edges 31. The orthodontic bracket 110 is provided as a front labial face 122 having a front edge 135, a bottom edge 137, an outer edges 133. The edges 131, 133, 135 and 137 in the preferred embodiment form a substantially outer rhomboidal configuration. Here again, the front surface 122 is provided with a layer 124 substantially identical to layer 24 with regard to the embodiment illustrated in FIGS. 1-3. In this embodiment, a substantial greater amount of surface area is provided which provides a greater surface area which is easier to visually view and provides longer, continuous alignment edges.

Figure 5:
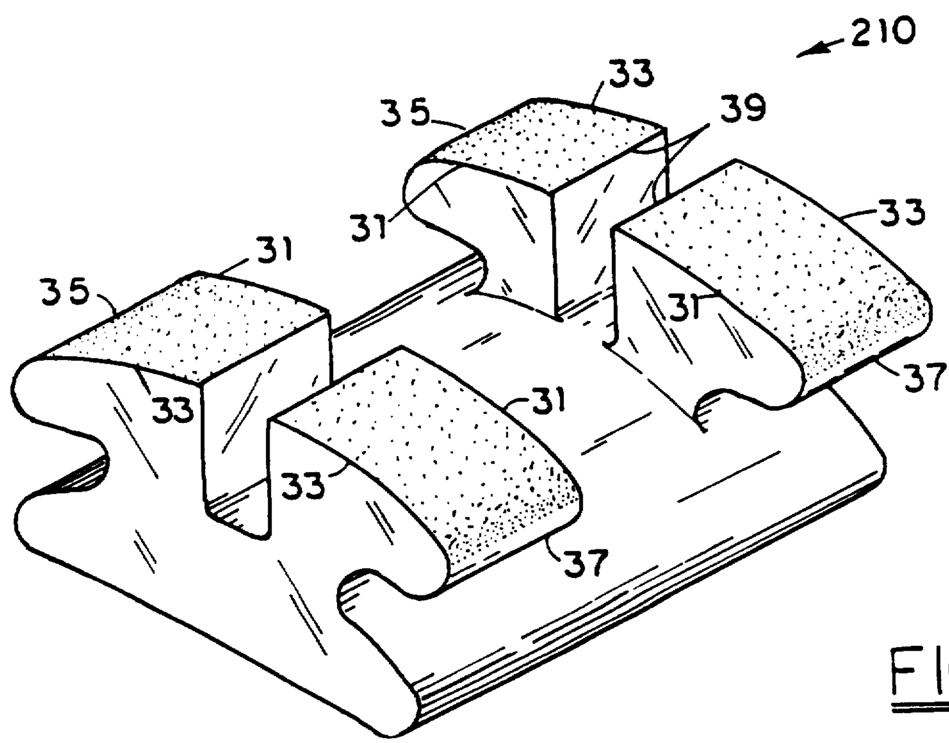
FIG. 5 is a perspective view of yet another modified embodiment of an orthodontic bracket made in accordance with the present invention.
Figure 5A:
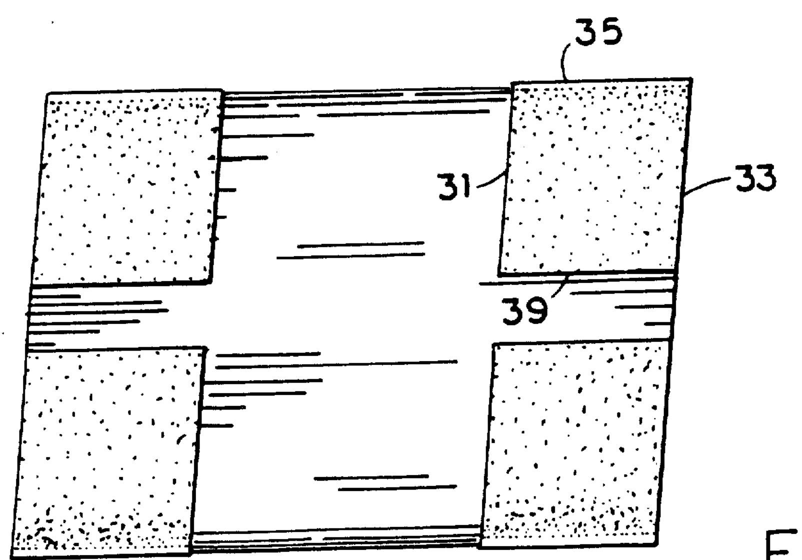
FIG. 5A is a front elevational view of the bracket of FIG. 5.

Referring to FIG. 5, there is illustrated yet another modified embodiment of an orthodontic bracket 210 made in accordance with the present invention. Like numerals, again representing like parts. In this embodiment, the orthodontic bracket is similar to that illustrated in FIGS. 1-3, except the connecting portion 15 is omitted. However, the bracket still has 31, 33, 35, 37, and 39.

Figure 6:
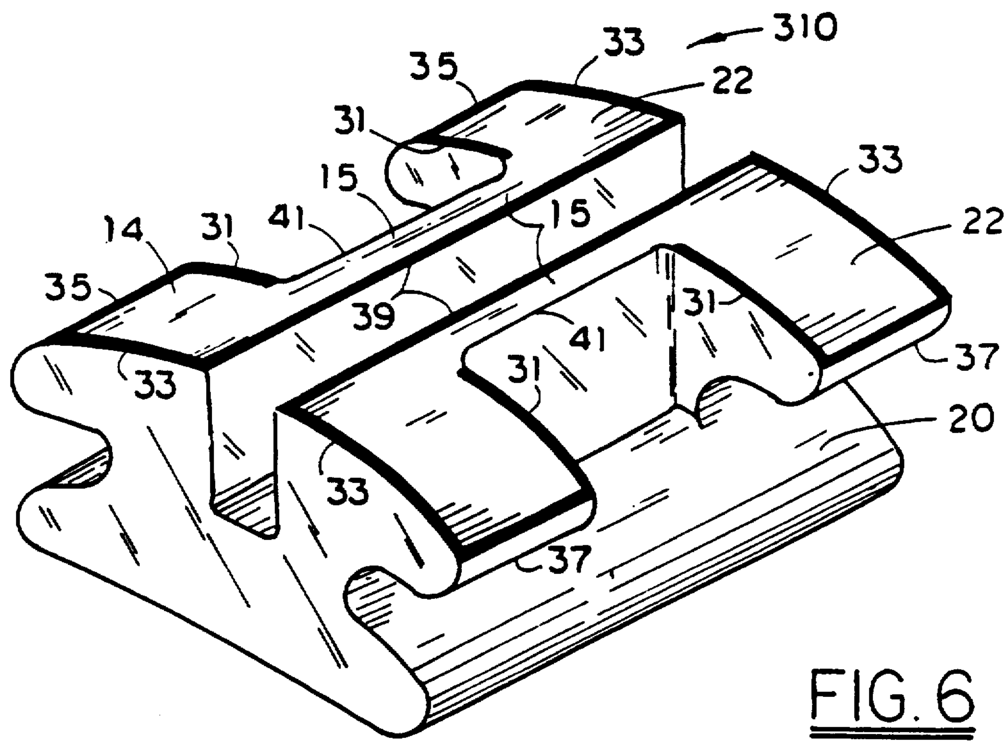
FIG. 6 is a perspective view of still another modified embodiment of an orthodontic bracket made in accordance with the present invention.
Figure 6A:
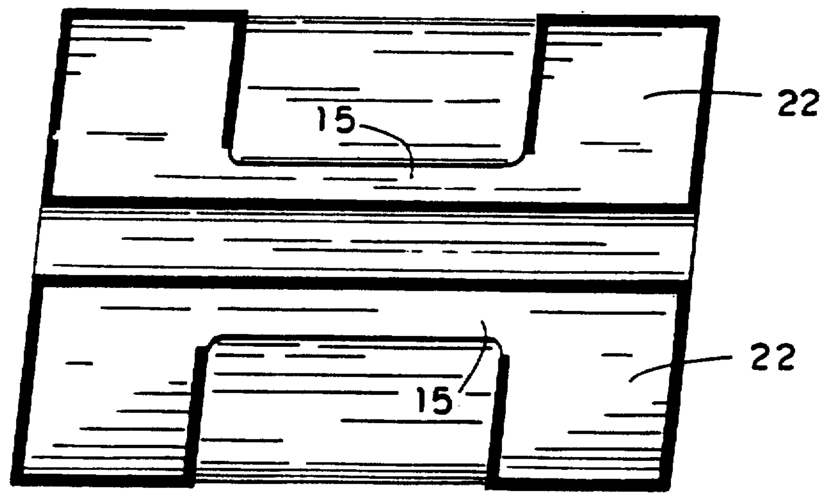
FIG. 6A is a front elevational view of the bracket of FIG. 6.

In the preferred embodiment illustrated, the entire area within the perimeter of the alignment edges is coated with removable layer 24. However, the present invention is not so limited, as other means may be provided to visually enhance the appearance of the alignment edges, for example, a narrow removable band or strip 311 of dye that may be placed adjacent the alignment edges 31, 33, 35, 37 so as to form an outline of the perimeter and/or desired alignment edges as illustrated in FIG. 6. Here again like representing like parts. As can be seen, a portion of the perimeter of face 22 of bracket 310 is not outlined with strip 311.

The removable layer or narrow band in the present embodiment may be applied in any desired fashion. In the preferred embodiment, the removable layer comprises a coating of a non-toxic ink applied by a roller, sprayer or brush. However, the present invention is not so limited.

In order to more fully understand the orthodontic bracket of the present invention and its use, Applicant will now discuss in detail how the bracket is applied. First, a bracket according to one of the embodiments as illustrated in FIGS. 1-6 is obtained. The removable layer 24 or outline will have preferably already been applied to the front labial face of the bracket, or is applied at that time. The bracket will have at least an alignment edge for alignment with each of the reference planes. The bracket is then secured to the tooth in the desired manner. For example, but not limited to, applying the appropriate adhesive to the tooth contact surface of the bracket 10. The bracket is then properly aligned and secured to the tooth. The reference edges 31, 33 aid the orthodontist in aligning the bracket with the long longitudinal axis y—y of the tooth and the edges 39, 41 and 35 assist in aligning the bracket with the occlusal plane x—x of the patient. The colored removable layer provides visual enhancement of the alignment edges so that alignment edges can be more distinctly and readily viewed. Once the orthodontic bracket has been located and properly positioned, it is secured to the tooth. The removable layer 24 is then removed, thus restoring the aesthetic quality of bracket will not be diminished. In the particular embodiment illustrated, the layer 24 is a water-soluble dye which is simply removed by applying water. In the particular embodiment illustrated, a light rubbing action in addition to the water will cause the dye to be easily removed from the front labial surface 22.

It is to be understood that various changes and/or modifications may be made without departing from the scope of the present invention. For example, but not by way of limitation, other non-toxic means may be applied to the front labial surface of the bracket such as a non-aqueous based ink which can be removed from the tooth by the application of an ethanol rinse having about 10% to 30% ethanol. Additionally, the present invention is not limited to the application of inks. A decal having the approximate configuration may be placed on the front labial surface of the bracket with an appropriate tack adhesive. After installation of the bracket on the tooth, the decal would simply be peeled off and the bracket cleaned. The present invention, in addition to being applicable to brackets having edges designed to align with predetermined reference planes, the present invention may be adopted for use with brackets which do not have edges which align with reference planes, such as the tooth long axis or occlusal plane. In such situations, the layer will be configured such that it provides the appropriate alignment edges for alignment with the reference plane. Thus, a bracket which does not have any reference edges can be easily and economically modified by the application of colored layer having edges which align with the long axis or occlusal plane of the patient. Typically the layer would have a generally rhomboidal outer configuration.

It is to be understood that various modifications and changes may be made to the present invention without departing from the scope of the present invention, the present application being limited by the following claims.

What is claimed is:

1. An orthodontic bracket for placement on a tooth of a patient, said bracket having a recess for receiving an orthodontic arch wire or other orthodontic appliance and having an outer labial surface capable of contacting the inside lips of the patient during use, said outer labial surface having at least one reference edge for alignment with the occlusal plane of the patient and at least one second reference edge for alignment with the longitudinal axis of said tooth on which said bracket is to be placed, removable means placed on said outer labial surface for enhancing the visual contrast of said first and second reference edges with respect to said tooth so as to enhance the visibility of said first and second reference edges of said bracket with respect to said tooth.

2. An orthodontic bracket according to claim 1 wherein said removable means comprises a coating layer of a removable colored water-soluble ink placed on substantially the entire outer labial surface.

3. An orthodontic bracket according to claim 2 wherein said removable colored water-soluble ink is black in color.

4. An orthodontic bracket according to claim 1 wherein said bracket is made of a material which is transparent.

5. An orthodontic bracket according to claim 1 wherein said means comprises a narrow strip of color placed along said at least one reference edge and said at least one second reference edge.

6. An orthodontic bracket according to claim 1 wherein said bracket is made of a material which is translucent.

7. An orthodontic bracket according to claim 1 wherein said bracket is made of a material having a color substantially the same as said tooth.

8. An orthodontic bracket having a visual appearance which is difficult to distinguish from said tooth, comprising: said bracket having a recess for receiving an orthodontic arch wire or other orthodontic appliance and having an outer labial surface capable of contacting said inner surface of the lips of the patient during use, said outer labial surface having an outer perimeter having at least one reference edge for alignment with a first reference plane and at least one second reference edge for alignment with a second reference plane; and removable means placed on said outer labial surface for enhancing the visual contrast of said first and second reference edges of said bracket with respect to said tooth.

9. An orthodontic bracket according to claim 8 wherein said bracket is made of a transparent type material.

10. An orthodontic bracket according to claim 9 wherein said bracket is made of a polycrystalline material.

11. An orthodontic bracket according to claim 8 wherein said bracket is made of a translucent type material.

12. A method of making an orthodontic bracket comprising the steps of:

(a) providing an orthodontic bracket having a recess for receiving an orthodontic arch wire or other orthodontic appliance and having an outer labial surface capable of contacting said inner surface of the lip of the patient during use, said outer labial surface having at least one reference edge for alignment with a first reference plane and at least one second reference edge for alignment with respect to a second reference plane; and (b) placing removable means on said outer labial surface or enhancing the visibility of said first and second reference edges of said bracket.

13. A method according to claim 12 wherein said coating layer is a non-toxic ink applied on substantially the entire outer labial surface.

14. A method of installing an orthodontic bracket on a tooth of a patient, said orthodontic bracket having a recess for receiving an orthodontic arch wire or other orthodontic appliance and having an outer labial surface capable of contacting said inner surface of the lips of the patient during use, said outer labial surface having at least one reference edge for alignment with a first reference plane and at least one second reference edge for alignment with a second reference plane, said bracket having removable means for enhancing the visibility of said first and second reference edges of said bracket with respect to said tooth, comprising of the steps of:

(a) securing said orthodontic bracket on the tooth of a patient using said first and second reference edges of said bracket for alignment with said first and second reference planes, respectively; and (b) removing said removable means for enhancing the visibility of said outer labial surface with respect to said tooth.

15. A method according to claim 14 wherein said removable means comprises a water-soluble ink.

16. A method according to claim 15 wherein said ink is removed by the application of a water rinse.

17. An orthodontic bracket for placement on a tooth of a patient having a recess for receiving an orthodontic arch wire or other orthodontic appliance and having an outer labial surface capable of contacting said inner surface of the lips of the patient during use, said outer labial surface having a plurality of reference edges for alignment with a first reference plane and a plurality of second reference edges for alignment with a second reference plane, removable means are provided on said outer labial surface for enhancing the visibility of the entire front face of said orthodontic bracket so as to render visually distinct said first and second reference edges of said bracket.

18. An orthodontic bracket according to claim 17 wherein said means for enhancing the visibility of said outer labial surface comprises a layer of a water-soluble non-toxic ink placed substantially on the entire outer labial surface.

19. An orthodontic bracket for placement on a tooth of a patient, said bracket having a recess for receiving an orthodontic arch wire or other orthodontic appliance and having a front labial surface capable of contacting said inner surface of the lip of the patient during use, removable means are provided on said front labial face for providing at least one first reference edge for alignment with a first reference plane of the tooth of the patient and at least one second reference edge for alignment with a second reference plane of the tooth of the patient.

20. An orthodontic bracket according to claim 19 wherein said removable means on said outer labial surface comprises a layer of removable ink.

21. An orthodontic bracket for placement on a tooth of patient, said bracket having a recess for receiving an orthodontic arch wire or other orthodontic appliance and having an outer labial surface capable of contacting the inside surface of the lips of the patient during use, said front labial surface having at least one reference edge for alignment with the occlusal plane of the patient and at least one second reference edge for alignment with the longitudinal axis of the tooth upon which the bracket is to be placed, removable ink means placed on said outer labial surface for enhancing the visual contrast of said first and second reference edges with respect to said tooth so as to enhance the visibility of said first and second reference edges of said bracket with respect to said tooth.

22. An orthodontic bracket according to claim 21 wherein substantially the entire outer labial surface is covered with said removable ink means.

23. An orthodontic bracket according to claim 21 wherein bracket has a plurality of referenced edges for alignment with said occlusal plane and a plurality of referenced edges for alignment with the longitudinal axis of the tooth, said removable ink means enhancing the visibility of said plurality of referenced edges for alignment with said longitudinal axis of said tooth and said occlusal plane.

* * * * *